United States Patent
Najafi et al.

(10) Patent No.: US 8,267,863 B2
(45) Date of Patent: Sep. 18, 2012

(54) PROCEDURE AND SYSTEM FOR MONITORING A PHYSIOLOGICAL PARAMETER WITHIN AN INTERNAL ORGAN OF A LIVING BODY

(75) Inventors: Nader Najafi, Ann Arbor, MI (US); Sonbol Massoud-Ansari, El Dorado Hills, CA (US); Catherine Hook Morgan, Ann Arbor, MI (US)

(73) Assignee: Integrated Sensing Systems, Inc., Ypsilant, MI (US)

( * ) Notice: Subject to any disclaimer, the term of this patent is extended or adjusted under 35 U.S.C. 154(b) by 1116 days.

(21) Appl. No.: 12/111,954

(22) Filed: Apr. 29, 2008

(65) Prior Publication Data

US 2008/0269573 A1 Oct. 30, 2008

Related U.S. Application Data

(60) Provisional application No. 61/009,190, filed on Dec. 26, 2007, provisional application No. 60/937,323, filed on Jun. 28, 2007, provisional application No. 60/926,713, filed on Apr. 30, 2007.

(51) Int. Cl. *A61B 5/07* (2006.01)
(52) U.S. Cl. .................................... 600/302
(58) Field of Classification Search ............... 600/302
See application file for complete search history.

(56) References Cited

U.S. PATENT DOCUMENTS

| | | |
|---|---|---|
| 4,023,562 A | 5/1977 | Hynecek et al. |
| 4,114,606 A | 9/1978 | Seylar |
| 4,566,456 A | 1/1986 | Koning et al. |
| 4,846,191 A | 7/1989 | Brockway et al. |
| 4,886,064 A | 12/1989 | Strandberg |
| 4,915,113 A | 4/1990 | Holman |
| 5,067,491 A | 11/1991 | Taylor, II et al. |
| 5,300,107 A | 4/1994 | Stokes et al. |
| 5,337,747 A | 8/1994 | Neftel |
| 5,535,752 A | 7/1996 | Halperin et al. |
| 5,558,640 A | 9/1996 | Pfeiler et al. |
| 5,706,565 A | 1/1998 | Sparks et al. |
| 5,853,422 A | 12/1998 | Huebsch et al. |
| 6,024,704 A | 2/2000 | Meador et al. |
| 6,120,457 A | 9/2000 | Coombes et al. |
| 6,201,980 B1 | 3/2001 | Darrow et al. |
| 6,268,161 B1 | 7/2001 | Han et al. |
| 6,309,350 B1 | 10/2001 | Van Tassel et al. |
| 6,328,699 B1 | 12/2001 | Eigler et al. |
| 6,442,413 B1 | 8/2002 | Silver |
| 6,636,769 B2 | 10/2003 | Govari et al. |
| 6,682,490 B2 | 1/2004 | Roy et al. |
| 6,746,404 B2 | 6/2004 | Schwartz |
| 7,147,604 B1 | 12/2006 | Allen et al. |
| 7,149,587 B2 | 12/2006 | Wardle et al. |
| 7,931,598 B2 * | 4/2011 | Bodecker et al. ............. 600/486 |
| 2003/0136417 A1 | 7/2003 | Fonsecca et al. |
| 2005/0065589 A1 * | 3/2005 | Schneider et al. ............ 607/126 |

FOREIGN PATENT DOCUMENTS

| | | |
|---|---|---|
| EP | 0812016 | 12/1997 |
| WO | WO0019888 | 4/2000 |
| WO | WO0030534 | 6/2000 |

OTHER PUBLICATIONS

Micromachined Planar Inductors on Silicon Wafers for MEMS Applications, Chong H. Ahn et al.; (Dec. 1998), IEEE Transaction on Industrial Electronics, vol. 45, No. 6, pp. 866-876.
A Passive Wireless Integrated Humidity Sensor, Timothy Harpster et al.; 2001, pp. 553-557.
Electrodeposited Copper Inductors for Intraocular Pressure Telemetry; R. Puers et al.; 2001 pp. 124-129.
Hermetically Sealed Inductor-Capacitor (LC) Resonator for Remote Pressure Monitoring; Eun-Chul Park et al.; Sep. 8, 1998; pp. 7124-7128.

* cited by examiner

*Primary Examiner* — Jerry Lin
(74) *Attorney, Agent, or Firm* — Hartman Global IP Law; Gary M. Hartman; Domenica N. S. Hartman (57) ABSTRACT

A system and surgical procedure for monitoring physiological parameters within an internal organ of a living body. The procedure entails making a first incision to expose the organ and a second incision through an external wall of the organ and into an internal cavity. A sensing unit is placed in the second incision such that a proximal end thereof remains outside the organ. The unit includes a sensing device having a sensing element for sensing the physiological parameter within the organ, and an anchor to which the sensing device is secured. The unit occludes the second incision and a distal end of the unit does not extend more than one centimeter into the cavity. The anchor is then secured to the wall of the organ, after which the first incision is closed and a readout device telemetrically communicates with the sensing device to obtain a reading of the physiological parameter.

58 Claims, 5 Drawing Sheets

PROCEDURE AND SYSTEM FOR MONITORING A PHYSIOLOGICAL PARAMETER WITHIN AN INTERNAL ORGAN OF A LIVING BODY

CROSS REFERENCE TO RELATED APPLICATIONS

This application claims the benefit of U.S. Provisional Application Nos. 60/926,713 filed Apr. 30, 2007, 60/937,323 filed Jun. 28, 2007, and 61/009,190 filed Dec. 26, 2007. The contents of these prior patent applications are incorporated herein by reference.

BACKGROUND OF THE INVENTION

The present invention generally relates to implantable medical devices, monitoring systems and associated procedures. More particularly, this invention relates to an implantable medical sensing unit, a sensing system, and a procedure for monitoring physiological properties of a living body, such as pressure, temperature, flow, acceleration, vibration, composition, and other properties of biological fluids within an internal organ.

Following open heart surgery in high risk patients, postoperative hemodynamic monitoring has been performed by pulmonary artery catheterization (PAC), which involves the insertion of a catheter into a pulmonary artery. The pulmonary artery catheter, often referred to as a Swan-Ganz catheter, allows for the measurement of pressures in the right atrium, right ventricle, pulmonary artery, and the filling ("wedge") pressure of the left atrium. However, a significant drawback of PAC is that the catheter is invasive, expensive, and carries morbidity.

More recently, various implantable devices have been developed to monitor and wirelessly communicate physiological parameters of the heart, as well as physiological parameters of other internal organs, including the brain, bladder and eyes. Such predicate wireless devices can generally be divided into two functional categories: large-sized (pacemaker-type) and smaller-sized telemetric devices. An example of a pacemaker-type wireless pressure sensor is the LVP-1000 Left Ventricular Pressure Monitoring System under development by Transoma Medical, Inc. The LVP-1000 comprises a sensor adapted to be implanted into an external wall of the heart, a wireless transmitting unit adapted to be located elsewhere within the patient, and wiring that physically and electrically connects the sensor and transmitting unit. The sensor of the LVP-1000 is adapted to be secured with sutures to the left side of the heart during an open-chest surgical procedure.

Smaller telemetric sensors include batteryless pressure sensors developed by CardioMEMS, Inc., Remon Medical, and the assignee of the present invention, Integrated Sensing Systems, Inc. (ISSYS). For example, see commonly-assigned U.S. Pat. Nos. 6,926,670 and 6,968,734 to Rich et al., and N. Najafi and A. Ludomirsky, "Initial Animal Studies of a Wireless, Batteryless, MEMS Implant for Cardiovascular Applications," Biomedical Microdevices, 6:1, p. 61-65 (2004). With such technologies, pressure changes are typically sensed with an implant equipped with a mechanical capacitor (tuning capacitor) having a fixed electrode and a moving electrode, for example, on a diaphragm that deflects in response to pressure changes. The implant is further equipped with an inductor in the form of a fixed coil that serves as an antenna for the implant, such that the implant is able to receive radio frequency (RF) signals from outside the patient and transmit the frequency output of the circuit. The implant can be placed with a catheter, for example, directly within the heart chamber whose pressure is to be monitored, or in an intermediary structure such as the atrial or ventricular septum.

Figure 1A:
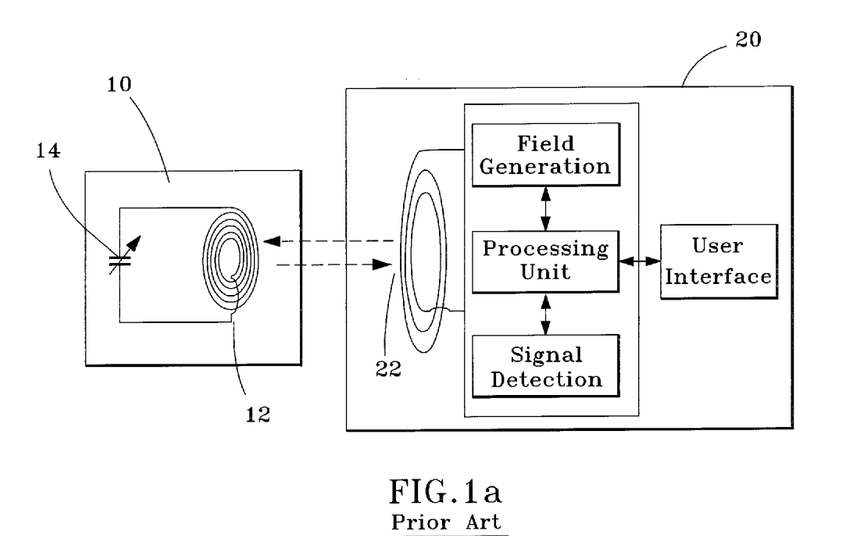
FIGS. 1a and 1b are block diagrams of wireless pressure monitoring systems that utilize resonant and passive sensing schemes, respectively, which can be utilized by monitoring systems of this invention.
Figure 1B:
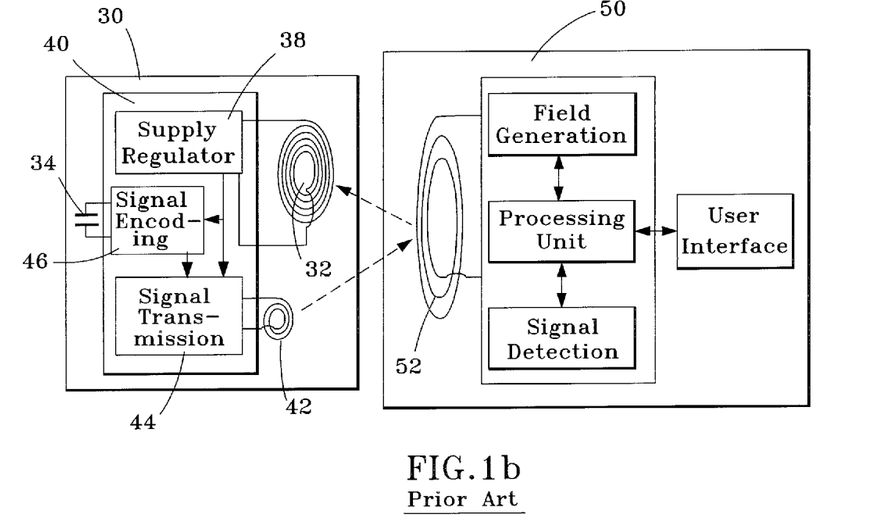

FIGS. 1a and 1b represent two types of wireless pressure sensing schemes disclosed in the Rich et al. patents. In FIG. 1a, an implant 10 is shown as operating in combination with a non-implanted external reader unit 20, between which a wireless telemetry link is established using a resonant scheme. The implant 10 contains a packaged inductor coil 12 and a pressure sensor in the form of a mechanical capacitor 14. Together, the inductor coil 12 and capacitor 14 form an LC (inductor-capacitor) tank resonator circuit that has a specific resonant frequency, expressed as $1/(LC)^{1/2}$, which can be detected from the impedance of the circuit. At the resonant frequency, the circuit presents a measurable change in magnetically-coupled impedance load to an external coil 22 associated with the reader unit 20. Because the resonant frequency is a function of the capacitance of the capacitor 14, the resonant frequency of the LC circuit changes in response to pressure changes that alter the capacitance of the capacitor 14. Based on the coil 12 being fixed and therefore having a fixed inductance value, the reader unit 20 is able to determine the pressure sensed by the implant 10 by monitoring the resonant frequency of the circuit.

FIG. 1b shows another wireless pressure sensor implant 30 operating in combination with a non-implanted external reader unit 50. A wireless telemetry link is established between the implant 30 and reader unit 50 using a passive, magnetically-coupled scheme, in which on-board circuitry of the implant 30 receives power from the reader unit 50. In the absence of the reader unit 50, the implant 30 lays passive and without any internal means to power itself. When a pressure reading is desired, the reader unit 50 must be brought within range of the implant 30.

In FIG. 1b, the implant 30 contains a packaged inductor coil 32 and a pressure sensor in the form of a mechanical capacitor 34. The reader unit 50 has a coil 52 by which an alternating electromagnetic field is transmitted to the coil 32 of the implant 30 to induce a voltage in the implant 30. When sufficient voltage has been induced in the implant 30, a rectification circuit 38 converts the alternating voltage on the coil 32 into a direct voltage that can be used by electronics 40 as a power supply for signal conversion and communication. At this point the implant 30 can be considered alert and ready for commands from the reader unit 50. The implant 30 may employ the coil 32 as an antenna for both reception and transmission, or it may utilize the coil 32 solely for receiving power from the reader unit 50 and employ a second coil 42 for transmitting signals to the reader unit 50. Signal transmission circuitry 44 receives an encoded signal generated by signal conditioning circuitry 46 based on the output of the capacitor 34, and then generates an alternating electromagnetic field that is propagated to the reader unit 50 with the coil 42.

The implant 30 is shown in FIG. 1b without a battery, and therefore its operation does not require occasional replacement or charging of a battery. Instead, the energy required to perform the sensing operation is entirely derived from the reader unit 50. However, the implant 30 of FIG. 1b could be modified to use a battery or other power storage device to power the implant 30 when the reader unit 50 is not sufficiently close to induce a voltage in the implant 30.

Small telemetric sensors of the types described above are adapted for implantation within the heart using a catheter or other minimally invasive outpatient technique, and not through the exterior wall of the heart during surgery.

BRIEF SUMMARY OF THE INVENTION

The present invention provides a system and surgical procedure for monitoring one or more physiological parameters within an internal organ of a living body. The system and procedure are particularly well-suited for performing short-term monitoring of organs such as the heart, brain, kidneys, lungs, bladder, etc., with a miniature implantable sensing device placed in an external wall of the organ, such as a wall of the heart, blood vessel, kidneys, lungs, bladder, etc., or a wall surrounding the organ, such as the abdominal wall or the meninges surrounding the brain. A particular but nonlimiting example is monitoring the left heart filling pressures for post-operative care of patients following open chest surgery, such as bypass surgery, heart valve surgery, and heart transplant surgery. In this regard, the present invention is intended to replace the need for postoperative pressure monitoring using such traditional invasive PAC techniques, subarachnoid devices used to monitor intracranial pressures, and other similar sensors.

A system and surgical procedure make use of at least one sensing unit adapted to be implanted in the living body and attached to an organ therein, and a readout device that is not adapted to be implanted in the living body. The sensing unit includes a sensing device having a sensing element adapted to sense the physiological parameter within the organ, and an anchor to which the sensing device is secured. The sensing unit is adapted for placement in an incision in an external wall of the organ so that a proximal end of the sensing unit is outside the organ, an oppositely-disposed distal end of the sensing unit does not extend more than one centimeter into the internal cavity, and the sensing unit occludes the incision. The readout device telemetrically communicates with the sensing device to obtain a reading of the physiological parameter.

The surgical procedure generally entails making a first incision in a living body to expose at least a portion of an internal organ of the living body. A second incision is then made through an external wall of the organ and into an internal cavity within which an internal physiological parameter is desired to be sensed. A sensing unit is then placed in the second incision such that a proximal end of the sensing unit is outside the organ. The sensing unit includes a sensing device having a sensing element adapted to sense the physiological parameter within the organ, and an anchor to which the sensing device is secured. The sensing unit is placed in the second incision so that a distal end of the sensing unit does not extend more than one centimeter into the internal cavity. The anchor is then secured to the external wall of the organ such that the sensing device is secured within the second incision by only the anchor and the second incision is occluded by only the sensing unit. The first incision can then be closed, after which a readout device located outside the living body is used to telemetrically communicate with the sensing device to obtain a reading of the physiological parameter.

The monitoring system and procedure are intended to be particularly well-suited for providing safe, fast, detailed, real-time, and continuous cardiac pressure measurements for short-term applications, such as during an operation (intraoperative) and postoperative monitoring over a period of hours, days or weeks in an emergency room or hospital. In cases where the patient is moved to a rehabilitation facility, the implant can be utilized for much longer periods and data relating to the physiological parameter(s) being monitored can be wirelessly sent to a physician or nurse in order to provide diagnostic tailored treatment of the patient. For patients that need even longer term monitoring, at-home monitoring can be easily accomplished by tying the readout device to the Internet, telephone, or other long-distance communication system. The wireless, batteryless operation of the sensing unit allows the unit to potentially function for a patient's lifetime with no maintenance or need for sensor replacement after initial implantation.

Miniaturization of the sensing unit can be effectively achieved by fabricating the sensing element as a miniature MEMS (micro-electromechanical system) sensor, combined with custom electronics and a telemetry antenna. Another preferred aspect of the invention is to limit the volume protrusion of the sensing unit into the cavity being monitored. In the case of the heart, the risk of thrombogenesis can be significantly reduced by limiting protrusion of the sensor unit into the blood stream within a heart chamber, in terms of distance into the cavity as well as shape and size of the protruding portion of the sensing unit. For this purpose, the sensing device is preferably configured so that the sensing element is located on a distal surface (relative to insertion direction) of the device, such that only the distal surface of the sensing device need contact the biological fluid being monitored.

Other objects and advantages of this invention will be better appreciated from the following detailed description.

BRIEF DESCRIPTION OF THE DRAWINGS

FIG. 3 schematically represents internal components of processing circuitry suitable for use in the sensing device of FIG. 2a.

FIG. 4 represents a perspective view of a cylindrical self-contained sensing device of the type represented in FIG. 2a.

FIG. 5 schematically represents the sensing device of FIG. 4 assembled with a dome-type anchor to form a sensing unit ready for implantation.

FIG. 6 schematically represents the sensing unit of FIG. 5 implanted in a wall of an internal organ in accordance with an embodiment of the invention.

DETAILED DESCRIPTION OF THE INVENTION

Illustrated in FIGS. 2a through 11 are monitoring systems and components thereof that implement one or more implantable sensors configured to be placed through an external wall of an internal organ for monitoring one or more physiological parameters within an internal cavity of the organ. Organs of particular interest include but are not limited to the heart, brain, kidneys, lungs, and bladder. Each system preferably makes use of a sensing unit that consists essentially of a sensing device and anchor, meaning that the sensing units lack a wire, cable, tether, or other physical component that conducts the output of the sensing device to a separate location where another component utilizes the output of the sensing device and/or transmits the output of the sensing device to a location outside the body of the patient. As such, the physical footprint of the implanted portion of the monitoring system can be limited to the sensing device and its anchor, such that the sensing unit is far smaller than, for example, the Transoma Medical, Inc., LVP-1000 Left Ventricle Pressure Monitoring System, which must be physically connected to a relatively large remote transmitting device.

Figure 2A:
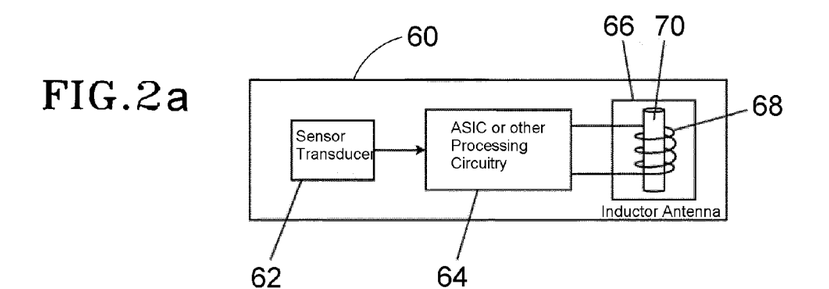
FIGS. 2a and 2b are schematic representations of a wireless sensing device and a readout device suitable for use in wireless monitoring systems of this invention.

While the resonant and passive schemes described in reference to FIGS. 1a and 1b are also within the scope of the invention, sensing devices of this invention are more preferably intended to translate a physiologic parameter into a frequency tone and modulate the impedance of an antenna with the frequency tone to communicate the physiologic parameter to an external readout unit. FIG. 2a represents a wireless implantable sensing device 60 as comprising a transducer 62, electronic circuitry 64 (e.g., an application specific integrated circuit, or ASIC), and an antenna 66. The antenna 66 is shown as comprising windings 68 (e.g., copper wire) wrapped around a core 70 (e.g., ferrite), though other antenna configurations and materials are foreseeable. The transducer 62 is preferably a MEMS device, more particularly a micromachine fabricated by additive and subtractive processes performed on a substrate. The substrate can be rigid, flexible, or a combination of rigid and flexible materials. Notable examples of rigid substrate materials include glass, semiconductors, silicon, ceramics, carbides, metals, hard polymers, and TEFLON. Notable flexible substrate materials include various polymers such as parylene and silicone, or other biocompatible flexible materials. A particular but nonlimiting example of the transducer 62 is a MEMS capacitive pressure sensor for sensing pressure, such as various blood pressures within the heart, intracranial pressure, intraocular pressure, etc., though other materials and any variety of sensing elements, e.g., capacitive, inductive, resistive, piezoelectric, etc., could be used. For example, the transducer 62 could be configured to sense temperature, flow, acceleration, vibration, pH, conductivity, dielectric constant, and chemical composition, including the composition and/or contents of a biological fluid, for example, oxygen, carbon dioxide, glucose, gene, hormone, or gas content of the fluid. The sensing device 60 may be powered with a battery or other power storage device, but in preferred embodiments is powered entirely by a readout device, such as a readout unit 80 represented in FIG. 2b.

Figure 2B:
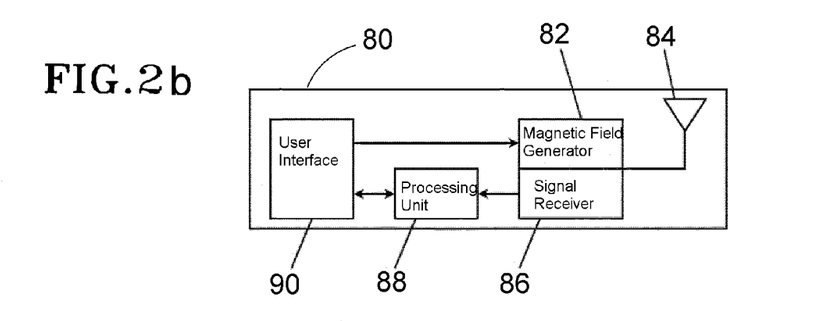

In addition to powering the sensing device 60, the readout unit 80 is represented as being configured to receive an output signal from the sensing device 60, process the signal, and relay the processed signal as data in a useful form to a user. The readout unit 80 is shown equipped with circuitry 82 that generates a high-frequency (e.g., 13.56 MHz), high-power signal for an antenna 84 to create the magnetic field needed in communicate with the sensing device 60. The readout unit 80 contains additional circuitry 86 to receive and demodulate a backscattered signal from the sensing device 60, which is demodulated and then processed with a processing unit 88 using calibration coefficients to quantify the physiological parameter of interest. The readout unit 80 is further shown as being equipped with a user interface 90, by which the operation of the readout unit 80 can be controlled to allow data logging or other user control and data examination.

Figure 3:
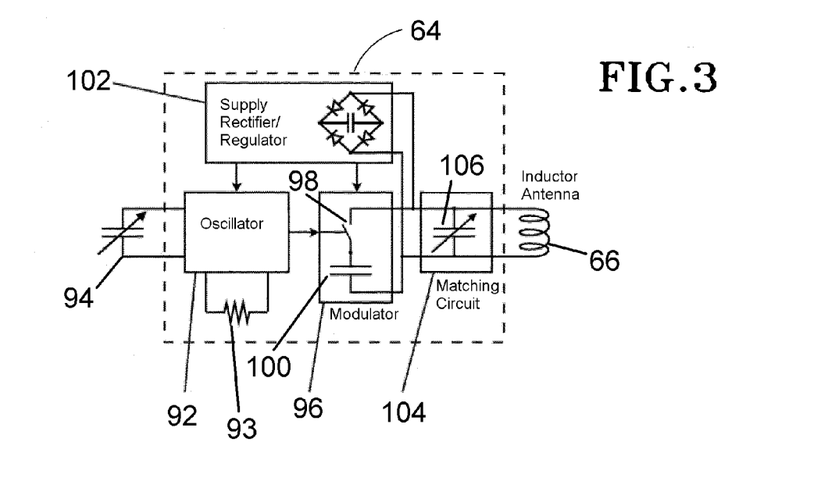

FIG. 3 represents a block diagram showing particularly suitable components for the electronic circuitry 64 of FIG. 2a. The circuitry 64 includes an oscillator 92, for example a relaxation oscillator, connected to a resistor 93 and a MEMs mechanical capacitor 94. A preferred MEMS capacitor 94 comprises a fixed electrode and a moving electrode on a diaphragm that deflects relative to the fixed electrode in response to pressure, such that the capacitor 94 is able to serve as a pressure sensing element for the transducer 62. A non-limiting example of a preferred MEMS capacitor 94 has a pressure range of about −100 to about +300 mmHg, with an accuracy of about 1 mmHg. Alternatively, a variable resistor transducer could be used with a fixed capacitance, or an inductor could be substituted for the transducer or fixed circuit element. Based on the RC or other time constant $(1/(LC)^{1/2})$, the oscillator 92 produces a frequency tone that directly relates to the capacitive value of the capacitor 94 and, therefore, the physiologic parameter of interest.

The circuitry 64 is further shown as including a modulator 96, with which the frequency tone of the oscillator 92 is encoded on a carrier frequency, placed on the antenna 66, and then transmitted to the readout unit 80. This is accomplished simply by opening and closing a switch 98 and adding a capacitance 100 to the antenna matching circuit, resulting in an AM (amplitude modulation) LSK (load shift keying) type modulation. This transmission approach is similar to that used in RFID (radio frequency identification) communications, except RFID does not typically encode analog information but instead encodes a few digital bits either on an AM LSK or FSK (frequency shift keying) modulation.

Because the preferred embodiment of the sensing device 60 does not utilize wires to transmit data or power, nor contains an internal power source, the circuitry 64 further includes a regulator/rectifier 102 to extract its operating power from an electromagnetic (EM) field, generated by the readout unit 80 or another EM power source. The regulator/rectifier 102 rectifies incoming power from the inductive antenna 66 and conditions it for the other circuit components within the circuitry 64. Finally, a matching circuit 104 is shown as comprising a trimmable capacitor bank 106 to resonate the inductor antenna 66, which is energized by the magnetic field and backscatters data as previously described.

As an alternative to the embodiment of FIG. 3, the modulator 96 could use a 13.56 MHz (or other frequency) magnetic field as a clock reference to create a second carrier frequency, such as one that is one-quarter or another sub-multiple or multiple of the original frequency. The second carrier frequency can then be amplitude modulated (AM) using the oscillator frequency tone and transmitted to the readout unit 80 via the same antenna 66. In this embodiment, the readout unit 80 may or may not have a second antenna to receive the second carrier frequency-based AM signal.

The communication scheme described above differs from resonate tank communication systems that use capacitive pressure transducer elements in conjunction with an inductor/antenna. In particular, the circuitry 64 allows the use of any frequency for the high power readout unit 80, which in preferred embodiments utilizes an industrial, scientific, medical (ISM) band frequency. In contrast, the frequencies and potentially large bandwidths required of resonate tank communication systems are subject to FCC emission limitations, likely requiring the use of extra shielding or potentially other measures taken in the facilities where the sensing device 60 and readout unit 80 are to be used. Another feature of the circuitry 64 is the allowance of more combinations of oscillator elements to be used. Because resonator tank systems require an inductive element and a capacitive element in which at least one of the elements serves as a transducer, resonator tank systems do not lend themselves well to resistive-based or other based sensors. Finally, the circuitry 64 also allows for signal conditioning, such as transducer compensation, which allows for such items as removing temperature dependence or other non-idealities that may be inherent to the transducer 62. In the preferred embodiment, a negative temperature coefficient of the MEMS capacitor 94 can be compensated with simple circuitry relying on the positive temperature coefficient of resistor elements arranged in a trimmable bank of two resistor units with largely different temperature coefficients that can be selectively added in a trimming procedure in production to select the precise level to compensate the transducer variation.

In the past, the restrictive levels of energy available to small implantable medical sensing devices and the desire to maximize data rates to capture more detailed physiological parameter response has been met with a robust type of analog communication that places information on the frequency rather than amplitude of the carrier. In U.S. Pat. No. 6,929,970 to Rich et al., a secondary carrier frequency is used for communication with an interrogator unit, resulting in a technique that consumes substantially more power in the implant and requires a second external antenna to receive the signal. The greater power consumption of the implant necessitates a tradeoff between smaller size and longer communication range. In contrast, the communication scheme described above for this invention draws upon the RFID-type communications, such as those described in U.S. Pat. Nos. 7,015,826 and 6,622,567, whose contents are incorporated herein by reference. However instead of communicating digital data using a fixed rate clock, the present invention transmits analog information as the frequency of the clock to lower power consumption and enhance powering and communication range. In this way, much of the readout unit 80 can utilize hardware that is commercially available for RFID, except that a different demodulator is required. An early example of RFID can be found in U.S. Pat. No. 4,333,072.

Figures 4, 5, 6:
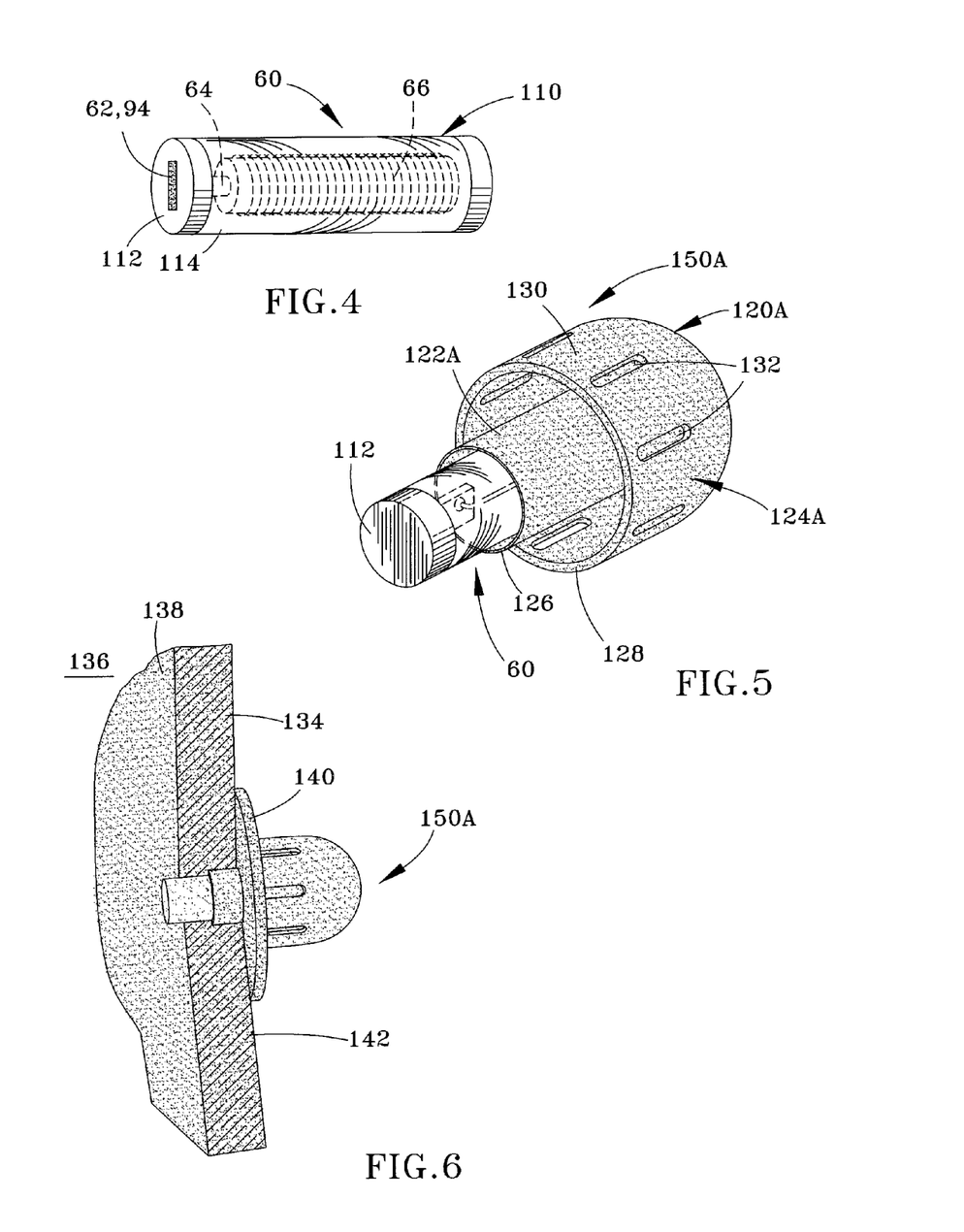
Figure 7:
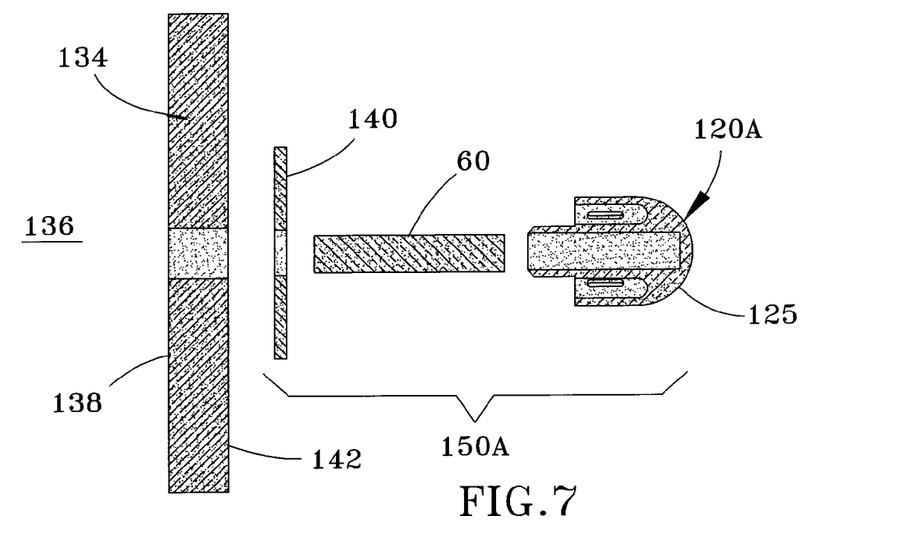
FIG. 7 schematically represents an exploded view of the sensing device of FIG. 5.

The transducer 62 (e.g., mechanical capacitor 94), the electronic circuitry 64 (including chips, diodes, capacitors, etc., thereof), the antenna 66 and any additional or optional components (e.g., additional transducers 62) of the sensing device 60 are preferably contained in a single sealed housing. FIG. 4 depicts a preferred example as being a cylindrical housing 110 having a flat distal face 112, though other shapes are also possible, for example, a torpedo-shape in which the peripheral face 114 of the housing 110 immediately adjacent the distal face 112 is tapered or conical (not shown). The housing 110 can be formed of glass, for example, a borosilicate glass such as Pyrex Glass Brand No 7740 or another suitably biocompatible material. A biocompatible coating, such as a layer of a hydrogel, titanium, nitride, oxide, carbide, silicide, silicone, parylene and/or other polymers, can be deposited on the housing 110 to provide a non-thrombogenic exterior for the biologic environment in which the sensing device 60 will be placed. As can be seen in FIG. 5, the inductive antenna 66 (comprising a copper coil 68 surrounding a ferrite core 70) occupies most of the internal volume of the housing 110. The size of the antenna 66 is governed by the need to couple to a magnetic field to enable telepowering with the readout unit 80 from outside the body, for example, a transmission distance of about 10 cm or more. The cylindrical shape of the housing 110 is convenient for the sensing device 60 to be placed with a conventional catheter, as well as anchors discussed in reference to FIGS. 5 through 11 below. The circuitry 64 is disposed between the antenna 66 and an end of the housing 110 that preferably carries the transducer 62. A nonlimiting example of an overall size for the housing 110 is about 3.7 mm in diameter and about 16.5 mm in length.

A preferred aspect of the invention is to locate the transducer 62 on a distal surface of the sensing device 60, for example, the flat distal face 112 of the cylindrical housing 110, or on the peripheral face 114 of the housing 110 immediately adjacent the distal face 112. In a preferred embodiment, the flat distal face 112 is defined by a biocompatible semiconductor material, such as a heavily boron-doped single-crystalline silicon, in whose outer surface the pressure-sensitive diaphragm (or other sensing element 94) is formed. In this manner, only the distal face 112 of the housing 110 need be in contact with a biological fluid whose physiological parameter is to be monitored. In the case of monitoring pressure within the heart, this aspect of the invention can be utilized to minimize protrusion of the sensing device 60 into the heart chamber, thereby reducing the risk of thrombogenesis.

FIGS. 5 through 11 represent different embodiments for anchors 120A, 120B, and 120C with which the sensing device 60 of FIG. 5 can be anchored to a wall of an internal organ, for example, by making an incision in the wall from the exterior of the organ, inserting the sensing device 60 in the incision, and then securing the sensing device 60 to the wall. Access to the organ can be through any suitable surgical procedure in which the desired implantation location is made accessible, such as by an open-chest surgical procedure including but not limited to bypass surgery, heart valve surgery, and heart transplant surgery. Together, the sensing device 60 and the anchor 120A, 120B or 120C form a sensing unit 150A, 150B, and 150C, respectively, that has minimal protrusion into the organ. Maximum protrusion of the sensing units 150A-C is preferably not more than one centimeter, more preferably not more than eight millimeters, for example between about 0.5 to about 2 millimeters, with a preferred volumetric protrusion of not more than about 0.02 cm$^3$. The distal end of the units 150A-C (for example, as defined by the distal face 112 of the housing 110 or the distal end of the anchor 120A-C) may also be slightly recessed below the internal surface of the wall, for example, up to about two millimeters from the internal surface of the wall. Particularly suitable materials for the anchors 120A-C include but are not limited to NITINOL, TEFLON, polymers such as parylene, silicone and PEEK, metals, glass, and ceramics. A nonlimiting example of an overall size for the anchors 120A-C is a maximum outer diameter of about 9.5 mm and longitudinal length of about 9 mm.

In FIGS. 5 through 8, the anchor 120A is configured to have a tubular portion 122A partially surrounded by a dome-shaped portion 124A. The sensing device 60 is axially disposed within the tubular portion 122A, such that the distal face 112 carrying the transducer 62 protrudes from an open end 126 of the tubular portion 122A. However, it is also within the scope of the invention that the distal face 112 of the sensing device 60 could be recessed within the anchor 120A such that the anchor 120A defines the distal end of the sensing unit 150A, or that the distal face 112 could be flush with the open end 126 of the anchor 120A. The sensing device 60 can be secured in the tubular portion 122A by any suitable means, such as an interference fit, a biocompatible epoxy, glue or cement, or any other type of attachment method or combinations of attachment methods known to those skilled in the art. The dome-shaped portion 124A generally joins the tubular portion 122A at an end 125 opposite the open end 126 of the tubular portion 122A through which the sensing device 60 is received. The dome-shaped portion 124A defines a substantially tubular section 130 that circumscribes the tubular portion 122A and terminates at an edge 128 short of the open end 126 of the tubular portion 122A. Multiple oblong openings 132 are defined in the tubular section to enable the anchor 120A to be secured to a wall of an internal organ, such as with standard surgical sutures or another suitable attachment technique that can be performed during the surgical procedure, such as nails, screws, springs, and biocompatible adhesives such as cements, glues, epoxies, etc.

Figure 8:
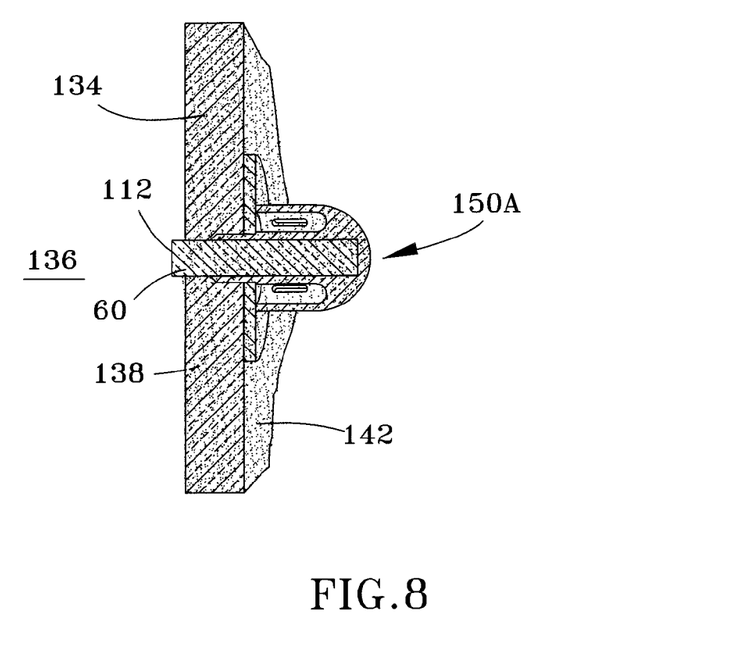
FIG. 8 schematically represents a cross-sectional view of the sensing unit of FIG. 5 implanted in a wall of an internal organ.

FIGS. 6 and 8 depict the sensing unit 150A of FIG. 5 implanted in an incision in a wall 134 of an internal organ for the purpose of sensing a physiological parameter of a biological fluid within an internal cavity 136 of the organ. The wall 134 may be an exterior wall of the heart, a blood vessel, kidneys, lungs, bladder, etc., or a wall surrounding an organ, such as the abdominal wall or the meninges surrounding the brain. As evident from FIG. 6, only the tubular portion 122A of the anchor 120A is inserted into the incision, and the dome-shaped portion 124A remains outside the incision; as such, the tubular and dome-shaped portions 122A and 124A are not configured to clamp the wall 134 therebetween. Furthermore, the anchor 120A does not protrude through the wall 134, but instead is recessed in the wall 134, whereas the distal end 112 of the sensing device 60 protrudes into an internal cavity of the organ. As noted above, the distance the distal end 112 protrudes from the internal surface 138 of the wall 134 (e.g., the endocardium lining a chamber of the heart) is preferably not more than one centimeter, and more preferably not more than eight millimeters. As also noted above, the sensing device 60 and anchor 120A could be configured so that the anchor 120A, and not the sensing device 60, protrudes beyond the wall 134, in which case the distal end 112 of the sensing device 60 may be recessed up to about two millimeters from the internal surface 138 of the wall 134. Again, the anchor 120A preferably does not protrude more than one centimeter, and more preferably not more than eight millimeters, beyond the internal surface 138 of the wall 134. Finally, it is within the scope of the invention that both the anchor 120A and the sensing device 60 could protrude into the internal cavity 136, or that neither the anchor 120A nor the sensing device 60 protrudes into the internal cavity 136, but instead are recessed in the wall 134.

FIGS. 6 and 8 further show the inclusion of a felt pad 140 between the peripheral edge 128 of the anchor 120A and the external surface 142 of the wall 134. A suitable material for the felt pad 140 is standard surgical grade felt. The anchor 120A and the felt pad 140 are then simultaneously attached (e.g., sutured) to the wall 134. Depending on the material from which it is formed, the felt pad 140 may be used to promote cell (tissue) growth and encapsulation of the incision, leading to further stabilization of the sensing unit 150A.

Figure 9:
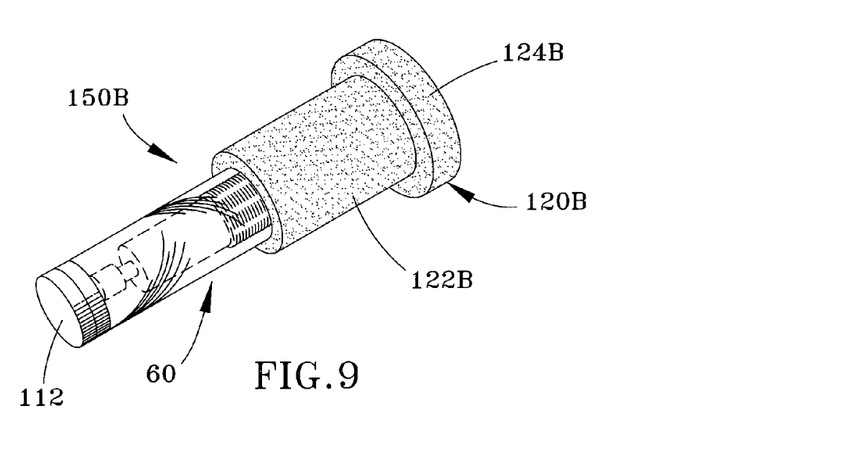
FIG. 9 schematically represents the sensing device of FIG. 4 assembled with a bolt-type anchor in accordance with another embodiment of the invention.
Figures 10, 11:
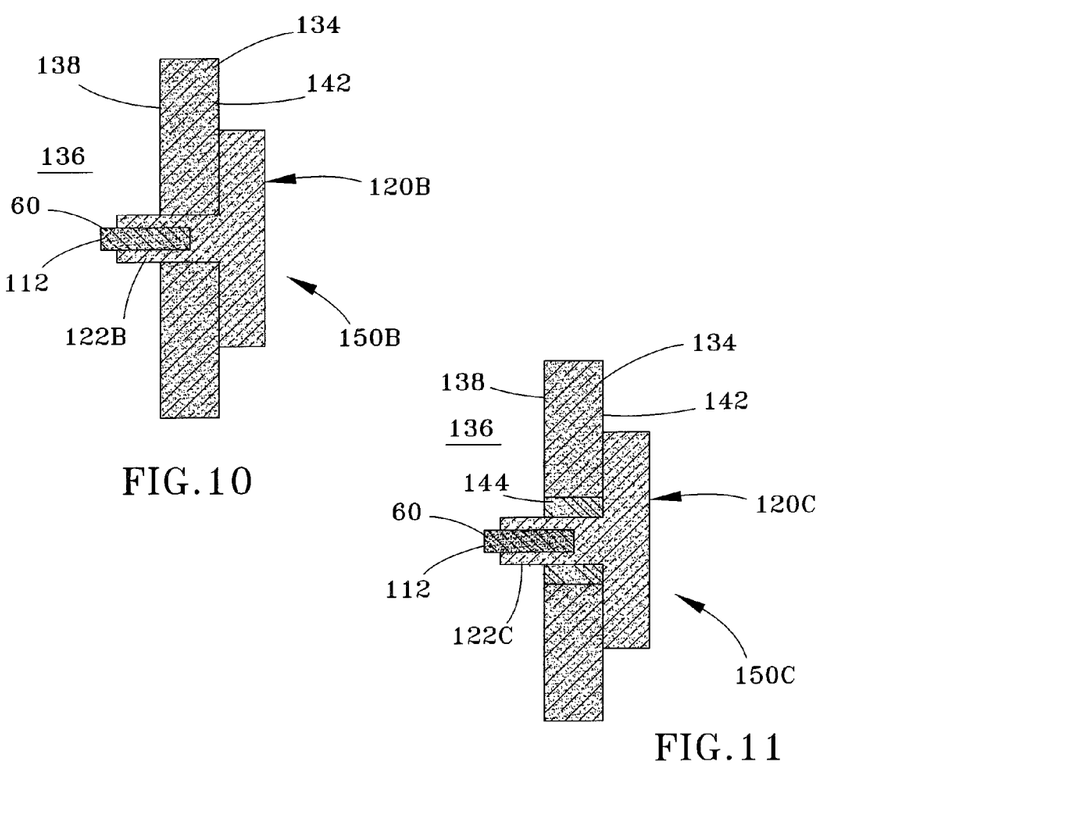
FIGS. 10 and 11 schematically represent sensing units equipped with alternative bolt-type anchors implanted in a wall of an internal organ.

In FIGS. 9 through 11, additional anchors 120B and 120C are again configured to have a tubular portion 122B/122C, but with a disk-shaped portion 124B/124C at one end thereof. As before, the sensing device 60 is shown axially disposed within the tubular portion 122B/122C, such that the distal face 112 carrying the transducer 62 protrudes from the tubular portion 122B/122C. Though not shown, the disk-shaped portion 124B/124C may be formed to have multiple oblong openings to enable the anchor 120B/120C to be secured to the wall 134 of an internal organ, such as with sutures or another suitable attachment technique that can be performed during the surgical procedure. Alternatively, the sensing unit 150C of FIG. 11 is shown as further including a tubular insert 144 that is secured in the incision prior to placement of the remainder of the unit 150C. The insert 144 can be attached to the wall 134 with an interference fit, or the use of a biocompatible cement, glue or epoxy, screws, springs, nails, etc. The tubular portion 122C of the anchor 120C can then be secured within the bore of the insert 144. A preferred aspect of this embodiment is that the anchor 120C is not permanently joined to the insert to facilitate exchange of the sensing unit 150C and/or its sensing device 60, and/or the use of a different anchor with additional features.

As evident from FIGS. 10 and 11, both the anchors 120B/120C and the sensing devices 60 protrude into the internal cavity 136, with the sensing devices 60 protruding farther, though any of the configurations discussed in reference to FIGS. 5 through 8 could also be present in the embodiments of FIGS. 9 through 11.

In addition to the above-noted features, the anchors 120A-120C could be modified to provide other features, for example, a device similar to an RFID tag can be added to the anchor such that it wirelessly transmits ID information concerning the sensing device 60. The ID information may include an ID number, ID name, patient name/ID, calibration coefficients/information, range of operation, date of implantation, valid life of the device (operation life), etc. The anchors 120A-120C may further include additional capabilities such as features for connection to a catheter, shunt, or other device (not shown).

To accurately locate the distal face 112 and its transducer 62 relative to the internal surface 138 of the wall 134, the thickness of the wall can be measured using one or more of the following procedures: an echocardiogram; a pressure-sensitive needle inserted through the desired location for the implant, wherein the pressure signal displays atrial waveforms when the needle reaches the inside of the heart; or estimation of the wall thickness by observation of the patient's size and weight. Based on the wall thickness, an appropriate combination of sensing device 60 and anchor 120A-C can be selected to achieve a desired placement of the transducer 62 relative to the internal surface 138 of the cavity 136. Thereafter, the incision is made at the desired location for the sensing device 60. For example, using standard devices and procedures, a tool can be inserted into the incision and a small circular portion (for example, about 3.5 mm diameter) of the heart wall is excised. The previously assembled sensing unit 150A-C (with the selected sensing device 60 and anchor 120A-C) is then inserted in the resulting circular hole, after which the anchor 120A-C and felt pad 144 (if used) are stitched to the wall 134, for example, sutured to the myocardium and pericardial layer of the heart.

In the case where the organ is the heart, the miniature sensing units of this invention are particularly useful when placed for sensing pressure in the left side of the heart (left atrium and left ventricle). For this purpose, two particular locations are especially of interest, the left atrial dome and the left ventricular apex, though other locations are also possible including the left and right atrial appendages. Of course, the sensing units of this invention are also useful for sensing pressures in other regions of the heart, including the right atrium and ventricle, in which case the sensing units may be placed in the right atrial dome, right ventricular apex, right atrial appendage, etc.

In addition to the sensing units 150A-C and reader unit 80 described above, the monitoring systems of this invention can be combined with other technologies to achieve additional functionalities. For example, the reader unit 80 can be implemented to have a remote transmission capability, such as home monitoring that may employ telephone, wireless communication, or web-based delivery of information received from the sensing units 150A-C by the reader unit 80 to a physician or caregiver. In this manner, the reader unit 80 can be adapted for remote monitoring of the organ and patient, closed-loop drug delivery of medications to treat the organ, closed-loop pacemaker parameter tuning to treat congestive heart failure or congestive heart failure related conditions, warning of critical worsening of congestive heart failure or congestive heart failure related conditions, portable or ambulatory monitoring or diagnosis, monitoring of battery operation, data storage, reporting global positioning coordinates for emergency applications, and communication with other medical devices chosen from the group consisting of pacemakers, left ventricular assist devices (LVAD), defibrillators, cardioverter defibrillators, drug delivery systems, non-drug delivery systems, and wireless medical management systems. Furthermore, the placement of the sensing units 15A-C can be utilized as part of a variety of different medical procedures, including early diagnosis of a heart failing due to congestive heart failure related conditions, early diagnosis of failure of the organ, early intervention in treatment of congestive heart failure related conditions, tailoring of medications, disease management, identification of complications from congestive heart failure related conditions, identification of complications from cardiovascular disease related conditions, treatment of complications from congestive heart failure related conditions, treatment of complications from cardiovascular disease related conditions, pacing adjustments to the heart, reduction in frequency and severity of hospitalizations due to cardiovascular diseases, reduction in frequency and severity of hospitalizations due to congestive heart failure, tuning of defibrillator or pacemaker parameters to improve congestive heart failure related conditions, identification of mitral valve stenosis, treatment of mitral valve stenosis, feedback regarding the impact of medication on the organ, and chronic disease management of the organ.

While the invention has been described in terms of specific embodiments, it is apparent that other forms could be adopted by one skilled in the art. Therefore, the scope of the invention is to be limited only by the following claims.

The invention claimed is:

1. A surgical procedure comprising:
    making a first incision in a living body to expose at least a portion of an internal organ of the living body, the organ having an internal cavity within which an internal physiological parameter is desired to be sensed;
    making a second incision through an external wall of the organ and into the internal cavity;
    placing a sensing unit in the second incision such that a proximal end of the sensing unit at a first extremity thereof is outside the organ and a distal end of the sensing unit at an oppositely-disposed second extremity thereof is within the internal cavity of the organ, the sensing unit consisting essentially of a sensing device having a sensing element adapted to sense the physiological parameter within the organ and an anchor to which the sensing device is secured, the anchor comprising first and second portions, the first portion of the anchor comprising a tubular housing in which the sensing device is housed and an open end adjacent the distal end of the sensing unit through which the sensing device is received into the tubular housing and through which the sensing element is exposed, either the first portion of the anchor or the sensing device defining the distal end of the sensing unit, the second portion of the anchor projecting radially from and surrounding the first portion, defining the proximal end of the sensing unit, and comprising means for securing the anchor to an external wall of the organ by engaging a proximal surface of the external wall disposed nearer the proximal end of the sensing unit and not engaging a distal surface of the external wall disposed nearer the distal end of the sensing unit, the sensing unit being placed in the second incision so that the second portion of the anchor, the securing means thereof, and the proximal end of the sensing unit defined thereby are outside the organ, and so that only the first portion of the anchor and the distal end of the sensing unit extend entirely through the external wall, the distal end of the sensing unit does not extend more than one centimeter into the internal cavity of the organ, and the first portion of the anchor occludes the incision; and
    securing the anchor to the external wall of the organ such that the sensing device is secured within the second incision by only the anchor and the second incision is occluded by only the first portion of the anchor;
    closing the first incision; and then
    telemetrically communicating with the sensing device to obtain a reading of the physiological parameter using a readout device located outside the living body.

2. The surgical procedure according to claim 1, wherein the organ is chosen from the group consisting of a heart, blood vessel, meninges, kidney, lung, bladder, and abdominal wall.

3. The surgical procedure according to claim 1, wherein the sensing device has a distal end, the sensing element is disposed at the distal end of the sensing device, and the distal end of the sensing device is recessed within the tubular housing of the first portion of the anchor such that the first portion of the anchor defines the distal end of the sensing unit.

4. The surgical procedure according to claim 1, wherein the sensing device has a distal end, the sensing element is disposed at the distal end of the sensing device, and the distal end of the sensing device protrudes from the tubular housing of the first portion of the anchor such that the sensing device defines the distal end of the sensing unit.

5. The surgical procedure according to claim 1, wherein each of the anchor and the sensing device has a distal end, the sensing element is disposed at the distal end of the sensing device, and the distal end of the sensing device is flush with the distal end of the anchor.

6. The surgical procedure according to claim 1, wherein the distal end of the sensing unit is recessed up to about two millimeters beneath an interior lining of the internal cavity, or is substantially flush with the interior lining, or extends into the internal cavity up to about eight millimeters beyond the interior lining.

7. The surgical procedure according to claim 1, wherein the anchor does not extend into the internal cavity.

8. The surgical procedure according to claim 1, wherein the surgical procedure is an open chest surgical procedure, the organ is a heart, the internal cavity is a chamber of the heart, the sensing device has a distal end at which the sensing element is disposed, and the distal end of the sensing unit is recessed up to about two millimeters beneath the endocardium lining the chamber, or is substantially flush with the endocardium, or extends into the chamber up to eight millimeters beyond the endocardium.

9. The surgical procedure according to claim 8, wherein the open chest surgical procedure is chosen from the group consisting of bypass surgery, heart valve surgery, and heart transplant surgery.

10. The surgical procedure according to claim 1, wherein the securing step comprises securing the second portion of the anchor to the external wall of the organ.

11. The surgical procedure according to claim 1, wherein the second portion of the anchor is semi-spherically dome-shaped, defines a wall that circumscribes and is spaced radially outward from the first portion of the anchor so as to define an annular gap therebetween, and an edge of the wall faces the external wall of the organ so as not to be exposed to other organs of the living body adjacent the organ.

12. The surgical procedure according to claim 1, wherein the second portion of the anchor is disk-shaped and oriented transverse to a longitudinal axis of the first portion.

13. The surgical procedure according to claim 1, further comprising the step of placing a felt pad between the second portion of the anchor and the external wall of the organ, and the securing step comprises simultaneously securing the felt pad and the anchor to the external wall of the organ.

14. The surgical procedure according to claim 1, wherein the first and second portions do not clamp the external wall therebetween.

15. The surgical procedure according to claim 1, further comprising the step of placing the sensing device in the first portion of the anchor prior to the placing step, and wherein the sensing unit consists of the sensing device and the anchor.

16. The surgical procedure according to claim 15, further comprising the step of securing the sensing device in the first portion of the anchor.

17. The surgical procedure according to claim 1, wherein the second portion of the anchor is secured to the external wall of the organ with biocompatible attachment means.

18. The surgical procedure according to claim 1, wherein the second portion of the anchor is secured to the external wall of the organ with sutures and a felt pad is secured with the sutures between the second portion of the anchor and the external wall of the organ.

19. The surgical procedure according to claim 1, wherein the second portion of the anchor has openings therein and the securing step comprises passing sutures through the openings and into the external wall of the organ.

20. The surgical procedure according to claim 19, wherein the second portion of the anchor comprises a cylindrical wall that circumscribes and is spaced radially outward from the first portion of the anchor so as to define an annular gap therebetween, and the openings are disposed in a distal edge defined by the cylindrical wall.

21. The surgical procedure according to claim 1, wherein the sensing device has a cylindrical shape with a distal end and an oppositely-disposed proximal end disposed within the anchor following the placing step, and the sensing element is at a distal surface defined by the distal end of the sensing device.

22. The surgical procedure according to claim 1, wherein the physiological parameter is at least one chosen from the group consisting of pressure, temperature, flow, acceleration, vibration, composition of a biological fluid, oxygen content of a biological fluid, carbon dioxide content of a biological fluid, glucose content of a biological fluid, gene content of a biological fluid, hormone content of a biological fluid, and gas content of a biological fluid.

23. The surgical procedure according to claim 1, wherein the physiological parameter is pressure.

24. The surgical procedure according to claim 23, wherein the sensing element comprises a diaphragm responsive to pressure within the internal cavity.

25. The surgical procedure according to claim 24, wherein the sensing device has a distal end and an oppositely-disposed proximal end disposed within the tubular housing of the first portion the anchor following the placing step, and the diaphragm is at a distal surface defined by the distal end of the sensing device.

26. The surgical procedure according to claim 1, wherein the sensing unit further comprises a telemetry antenna and the readout device comprises means for telemetrically communicating with the telemetry antenna of the sensing device and optionally means for electromagnetic powering of the sensing device.

27. The surgical procedure according to claim 26, wherein the telemetric communication between the sensing device and the readout device is established using a resonant scheme in which the sensing device telemetrically receives power from the readout device.

28. The surgical procedure according to claim 26, wherein the telemetric communication between the sensing device and the readout device is established using a passive scheme in which the sensing device telemetrically receives electromagnetic power from the readout device or a second separate device.

29. The surgical procedure according to claim 26, wherein the sensing unit further comprises processing circuitry for processing electrical communications between the sensing element and the telemetry antenna of the sensing unit.

30. The surgical procedure according to claim 29, wherein the processing circuitry causes the telemetry antenna of the sensing unit to transmit an amplitude modulation transmission to the telemetric communicating means of the readout device.

31. The surgical procedure according to claim 26, wherein the sensing device obtains power from a power storage device within the sensing unit.

32. The surgical procedure according to claim 1, wherein the sensing element comprises a micromachined structure.

33. The surgical procedure according to claim 1, wherein the surgical procedure is part of at least one of the following medical procedures: diagnosis of chronic diseases; diagnosis of a heart failing due to congestive heart failure related conditions; diagnosis of failure of the organ; intervention in treatment of congestive heart failure related conditions; tailoring of medications; disease management; identification of complications from congestive heart failure related conditions; identification of complications from cardiovascular disease related conditions; treatment of complications from congestive heart failure related conditions; treatment of complications from cardiovascular disease related conditions; pacing adjustments to the heart; reduction in frequency and severity of hospitalizations due to cardiovascular diseases; reduction in frequency and severity of hospitalizations due to congestive heart failure; tuning of defibrillator or pacemaker parameters to improve congestive heart failure related conditions; identification of mitral valve stenosis; treatment of mitral valve stenosis, feedback regarding the impact of medication on the organ; and chronic disease management of the organ.

34. The surgical procedure according to claim 1, wherein the readout device is used to perform at least one of the following:
remote monitoring of the organ and the living body, remote monitoring of the organ and the living body with a telephone-based data and information delivery system; remote monitoring of the organ and the living body with a wireless telephone-based data and information delivery system; remote monitoring of the organ and the living body with an Internet-based data and information delivery system; closed-loop drug delivery of medications to treat the organ; closed-loop pacemaker parameter tuning to treat congestive heart failure or congestive heart failure related conditions; warning of critical worsening of congestive heart failure or congestive heart failure related conditions; portable or ambulatory monitoring or diagnosis; monitoring of battery operation; data storage; reporting global positioning coordinates for emergency applications; and communication with other medical devices chosen from the group consisting of pacemakers, left ventricular assist devices, defibrillators, cardioverter defibrillators, drug delivery systems, non-drug delivery systems, and wireless medical management systems.

35. A system for monitoring a physiological parameter within an internal cavity of an internal organ of a living body, the system comprising:
    at least one sensing unit adapted to be implanted in the living body and attached to the organ therein, the sensing unit having a proximal end at a first extremity thereof and a distal end at an oppositely-disposed second extremity thereof, the sensing unit consisting essentially of a sensing device having a sensing element adapted to sense the physiological parameter within the organ and an anchor to which the sensing device is secured, the anchor comprising first and second portions, the first portion of the anchor comprising a tubular housing in which the sensing device is housed and an open end adjacent the distal end of the sensing unit through which the sensing device is received into the tubular housing and through which the sensing element is exposed, either the first portion of the anchor or the sensing device defining the distal end of the sensing unit, the second portion of the anchor projecting radially from and surrounding the first portion, defining the proximal end of the sensing unit, and comprising means for securing the anchor to an external wall of the organ by engaging a proximal surface of the external wall disposed nearer the proximal end of the sensing unit and not engaging a distal surface of the external wall disposed nearer the distal end of the sensing unit, the sensing unit being sized and configured for placement in an incision in the external wall of the organ so that the second portion of the anchor, the securing means thereof, and the proximal end of the sensing unit defined thereby are outside the organ, and so that only the first portion of the anchor and the distal end of the sensing unit extend entirely through the external wall, the distal end of the sensing unit does not extend more than one centimeter into the internal cavity of the organ, and the first portion of the anchor occludes the incision; and
    a readout device that is not adapted to be implanted in the living body, the readout device comprising means for telemetrically communicating with the sensing device to obtain a reading of the physiological parameter.

36. The system according to claim 35, wherein the sensing device has a distal end, the sensing element is disposed at the distal end of the sensing device, and the distal end of the sensing device is recessed within the tubular housing of the first portion of the anchor such that the anchor defines the distal end of the sensing unit.

37. The system according to claim 35, wherein the sensing device has a distal end, the sensing element is disposed at the distal end of the sensing device, and the distal end of the sensing device protrudes from the tubular housing of the first portion of the anchor such that the sensing device defines the distal end of the sensing unit.

38. The system according to claim 35, wherein each of the anchor and the sensing device has a distal end, the sensing element is disposed at the distal end of the sensing device, and the distal end of the sensing device is flush with the distal end of the anchor.

39. The system according to claim 35, wherein the second portion of the anchor is semi-spherically dome-shaped and defines a wall that circumscribes and is spaced radially outward from the first portion of the anchor so as to define an annular gap therebetween.

40. The system according to claim 35, wherein the second portion of the anchor is disk-shaped and oriented transverse to a longitudinal axis of the first portion.

41. The system according to claim 35, wherein the first and second portions are not configured to clamp the external wall therebetween.

42. The system according to claim 35, further comprising means for securing the second portion of the anchor to the external wall of the organ, the securing means being at least one biocompatible attachment device chosen from the group consisting of sutures, nails, screws, springs, and adhesives.

43. The system according to claim 35, wherein the sensing unit consists of the sensing device and the anchor.

44. The system according to claim 35, further comprising a felt pad and sutures for attaching the anchor to the external wall of the organ and securing the felt pad between the external wall and a portion of the anchor.

45. The system according to claim 44, wherein the anchor has openings therein adapted for passing sutures therethrough.

46. The system according to claim 45, wherein the anchor comprises a first portion adapted to be inserted into and occlude the incision and a second portion that surrounds the first portion and is not adapted to be inserted into the incision, and the openings of the anchor are disposed at an outer periphery of the second portion.

47. The system according to claim 35, wherein the sensing device has a cylindrical shape with a distal end and an oppositely-disposed proximal end disposed within the anchor, and the sensing element is at a distal surface defined by the distal end of the sensing device.

48. The system according to claim 35, wherein the physiological parameter is at least one chosen from the group consisting of pressure, temperature, flow, acceleration, vibration, composition of a biological fluid, oxygen content of a biological fluid, carbon dioxide content of a biological fluid, glucose content of a biological fluid, gene content of a biological fluid, hormone content of a biological fluid, and gas content of a biological fluid.

49. The system according to claim 35, wherein the physiological parameter is pressure.

50. The system according to claim 49, wherein the sensing element comprises a diaphragm responsive to pressure.

51. The system according to claim 50, wherein the diaphragm is at a distal surface of the sensing device.

52. The system according to claim 35, wherein the sensing unit further comprises a telemetry antenna, and the telemetric communicating means of the readout device is adapted to telemetrically communicate with the telemetry antenna of the sensing device and optionally electromagnetically power the sensing device.

53. The system according to claim 52, wherein the telemetric communication between the sensing device and the readout device is established using a resonant scheme in which the sensing device telemetrically receives power from the readout device.

54. The system according to claim 52, wherein the telemetric communication between the sensing device and the readout device is established using a passive scheme in which the sensing device telemetrically receives electromagnetic power from the readout device or a second separate device.

55. The system according to claim 52, wherein the sensing unit further comprises processing circuitry for processing electrical communications between the sensing element and the telemetry antenna of the sensing unit.

56. The system according to claim 55, wherein the processing circuitry causes the telemetry antenna of the sensing unit to transmit an amplitude modulation transmission to the telemetric communicating means of the readout device.

57. The system according to claim 52, wherein the sensing device contains a power storage device.

58. The system according to claim 35, wherein the sensing element comprises a micromachined structure.

* * * * *